(12) United States Patent
Jastrzebski et al.

(10) Patent No.: US 7,373,302 B1
(45) Date of Patent: May 13, 2008

(54) BRAIN SIGNAL SELECTION BY CONTRACTION MAPPING WITH ITERATED FUNCTION SYSTEMS

(76) Inventors: George Brinnig Jastrzebski, 824 McGuire Dr., Modesto, CA (US) 95355; Lowell R. Wedemeyer, 719 Yarmouth Rd., Suite 204, Palos Verdes Estates, CA (US) 90274-2673

( * ) Notice: Subject to any disclaimer, the term of this patent is extended or adjusted under 35 U.S.C. 154(b) by 0 days.

(21) Appl. No.: 08/201,352

(22) Filed: Feb. 24, 1994

Related U.S. Application Data

(63) Continuation-in-part of application No. 07/831,956, filed on Feb. 6, 1992, now abandoned, which is a continuation-in-part of application No. 07/405,331, filed on Sep. 11, 1989, now Pat. No. 5,218,530.

(51) Int. Cl.
*G06Q 99/00* (2006.01)
(52) U.S. Cl. .......................................... 705/1
(58) Field of Classification Search ........... 364/413.02, 364/413.05, 413.03, 413.06; 395/118, 140, 395/141, 924; 382/10, 56, 128, 181, 207; 128/731, 920, 922, 923; 705/3, 1; 600/301, 600/407; 345/419; 706/924
See application file for complete search history.

(56) References Cited

U.S. PATENT DOCUMENTS

| | | | | |
|---|---|---|---|---|
| 4,135,406 A | * | 1/1979 | Kretz | |
| 4,744,029 A | * | 5/1988 | Raviv et al. | ........... 364/413.05 |
| 4,941,193 A | * | 7/1990 | Barnsley et al. | ............... 382/56 |
| 5,065,447 A | * | 11/1991 | Barnsley et al. | ............... 382/56 |
| 5,201,321 A | * | 4/1993 | Fulton | |
| 5,218,530 A | * | 6/1993 | Jastrzebski et al. | ..... 364/413.05 |
| 5,365,941 A | * | 11/1994 | Yoshimatsu et al. | |
| 5,579,774 A | * | 12/1996 | Miller et al. | |

* cited by examiner

*Primary Examiner*—James P. Trammell
*Assistant Examiner*—Matthew Osborne
(74) *Attorney, Agent, or Firm*—Lowell R. Wedemeyer

(57) ABSTRACT

The invention is a device for adapting a computer to enable identification of those subsets of a stream of signal values which form patterns when contraction mapped to an approximation of the attractor of a fractal. The machine currently employs an approximation of the attractor of an affine Sierpinski gasket. In principle, the fractal could be a Sierpinski carpet, Menger sponge, the Mandelbrot Set, or fractals constructed in polar or spherical coordinates. The stream of signal values and subsets of the stream can be displayed, segregated, or otherwise processed automatically by computer by reference to the mapped locations of the signal values. Selection sets can be employed manually to confine a visualized pattern as displayed on the map. Signal values which contribute to the confined pattern then are automatically identified. Some selection sets can be pre-set to automatically confine mapped signal values which fall within certain pre-determined patterns without visual inspection and manual confinement. The subsets of signal values identified by the selection sets are then available for further processing, including display of segregated subsets. The device enables display of segregated subsets of signal values in other display and analysis modes, such as the graphic phase space portraits of U.S. Pat. No. 5,218,530.

32 Claims, 11 Drawing Sheets

GRAPHIC IMAGE 1

GRAPHIC IMAGE 2

GRAPHIC IMAGE 3

GRAPHIC IMAGE 4

GRAPHIC IMAGE 5

GRAPHIC IMAGE 6

BRAIN SIGNAL SELECTION BY CONTRACTION MAPPING WITH ITERATED FUNCTION SYSTEMS

CROSS-REFERENCES TO RELATED APPLICATIONS

This is a continuing-in-part application based upon application Ser. No. 07/831,956, filed Feb. 6, 1992, now abandoned, which is a continuing in part application based upon application Ser. No. 07/405,331 of GEORGE B. JASTRZEBSKI and LOWELL R. WEDEMEYER, for A METHOD OF DISPLAYING AND ANALYZING NON-LINEAR, DYNAMIC BRAIN SIGNALS, filed Sep. 11, 1989, and upon which U.S. Pat. No. 5,218,530 issued to the same applicants on Jun. 8, 1993. Said U.S. patent of the Applicants hereby is incorporated herein by this reference.

STATEMENT AS TO RIGHTS TO INVENTIONS MADE UNDER FEDERALLY-SPONSORED RESEARCH AND DEVELOPMENT

No federally-sponsored research and development is involved.

BACKGROUND OF THE INVENTION

1. Field of the Invention

The field of the invention is analysis of a stream of signal values by pattern detection and selection, and in particular, the display and analysis of electroencephalic signal values by mapping, pattern identification, and pattern confinement.

2. Description of Related Art

A great body of evidence suggests that electromagnetic signals recorded from the human head reflect brain function and other physiologic processes. Recording and analysis of such signals have been conducted by computer because of the high speed of brain events, the electromagnetic character of the values measured, and the great volume of signal values. It is essential to segregate the signal values detected by electrodes on the human scalp into subsets because a wide variety of sources contribute to the signal values, including multiple sources from within the brain, as well as signals from muscles such as those in the head and neck. In addition, there may also be contributions to the signals from external sources such as the computer itself, other electric appliances, and electric wiring.

Typically in current practice, a variety of electronic filters and mathematical averaging methods have been employed to pre-process the computer-recorded stream of signal values to eliminate "noise" and "artifact". Signal values which fell too far outside rather arbitrary limits were rejected as "artifacts", which were viewed as "distorting" the signal. The "noise" was viewed as impossible to analyze and thus assumed to have no meaning for the simple reason that no means of interpreting it was known. Thus, an initial subset of signal values was obtained by "filtering out" and discarding "noise" and "artifact", leaving for analysis those values which were presumed to represent the "true" signal.

The pre-processing done in current practice imposes a conceptual paradigm upon the stream of signal values which then shapes all subsequent analysis of the signal values. A wave function is the dominant historic conceptual paradigm according to which electromagnetic signals recorded from the brain have been "transformed" or "inverted". The resulting analytic display of the transformed stream of signal values is referred to in common parlance as "brain waves". Typically the analytic wave function of choice was the sine wave employed in a Fourier Transform and implemented on a digital computer as a Fast Fourier Transform or FFT, though sometimes a Mellin or "double" Fourier Transform was used. Due to well-recognized limitations of the Fourier Transform and "wave" paradigms, new conceptual paradigms have been sought to analytically transform computer-recorded streams of signal values which can be presented as meaningfully segregated subsets. More recently, wavelet transforms have been employed with a wide variety of signals, including electrophysiologic signals as well as sound and other vibrational signal forms.

Ideally, a conceptual paradigm should enable mathematically-reversible transformations which index a stream of signal values into meaningful subsets from which one can infer a causal relation to body function or to external stimuli, and thus decompose the stream of signal values into subsets, or component signal 'events', for which a causal relationship can be empirically sought. The difficulty of indexing a raw stream of signal values into meaningful subsets is referred to as the "inverse problem".

Applicants' U.S. Pat. No. 5,218,530 applies modern mathematics of chaos, non-linear dynamics and phase space portraits to display a stream of raw signal values from scalp electrodes for the purpose of visually detecting patterns in the stream of signal values. It then employs computer-implemented selection sets to segregate the subsets of signal values which contribute to the visually identified pattern. Some examples of implementation of "selection setst" within drawings displayed on a computer monitor is exemplified by AutoCAD Reference Manual, July 1986, copyright Autodesk, Inc., Sec. 2.10, pp. 45-49. AutoCAD is a registered trademark of Autodesk, Inc.

The instant invention employs the 'chaos game' for contraction mapping of streams of signal values to deterministic fractals which are defined as the attractors of Iterated Function Systems. In principle, the method could also be adapted to probabilistic Iterated Function Systems, though the present implementation does not do so. The mapped signal values then are searched for patterns. When a pattern is detected is confined, or encompassed, by an exclusive "selection set". The confined subset of signal values then automatically is segregated from the stream of signal values by computer.

Some background of art related to the 'chaos game' and to contraction mapping to deterministic fractals with Iterated Function Systems follows.

Modern mathematics of topology and fractals are explained in *Fractals for the Classroom*, by Heinz-Otto Peitgen, Hartmut Jurgens, and Dietmar Saupe, published by Springer-Verlag, New York, 1992, ISBN 0-387-97041-X. Deterministic fractals called the Sierpinski gasket and the Sierpinski carpet are defined, id., at chapter 2.2, pp. 91-95, and methods of indexing them with addresses are defined id., at chapter 2.7, pp. 128-127; chapter 2.10, pp. 148-150; chapter 6.2, pp. 330-338. The Menger sponge deterministic fractal is defined, id., at p. 124 and 131-132. More detailed application of the "chaos game" and use of probabilities in its implementation in computer programming, are discussed in Peitgen, H.-O.; Jurgens, H.; and Saupe, D; Chaos and Fractals, New Frontiers of Science, Springer-Verlag, New York, 1992, Chap. 6, pp. 297-352.

The terms "deterministic fractal" and "Iterated Function System" sometimes are used nearly interchangeably. It should be understood, however, that an Iterated Function System is a process, usually though not always implemented on a computer, to approximate a mathematically precise object called a deterministic fractal. The deterministic fractal is the theoretical limit object resulting from an infinite number of iterations of the Iterated-Function System. The "deterministic fractal" therefore is called the "attractor" of the iterative process called the "Iterated Function System".

An algorithm called the 'chaos game' for generating the Sierpinski gasket with random numbers is defined, id., at chapter 1.3 at pp. 41-43. More general use of the 'chaos game', using random numbers to map a variety of fractal forms as attractors of Iterated Function Systems ("IFS"), is explained, id., at chapter 6.2, p. 339-344. Methods of defining and generating Iterated Function Systems are described, id., at Chapter 5, pp. 255-318. The "contraction mapping principle" is explained, id. at Chapter 5.5, pp. 284-293, and especially at p. 287. Deterministic fractals such as the Sierpinski gasket, Sierpinski carpet and Menger sponge can be viewed as attractors of Iterated Function Systems. In addition, these attractors are universal indices for certain topologic classes of objects. Id., at Chapter 2.7, pp. 128-137. This means, in a topologic sense, that these attractors contain, or index, within themselves an enormous collection of mathematically distinct, but less complex, attractors. Id. That is, the attractors of these deterministic fractals are themselves constructed of less-complex attractors.

The Mandelbrot set, M, may be viewed as an attractor of an Iterated Function System. The Mandelbrot set also may be viewed as a universal index of topologic entities within the mathematical class called Julia Sets. Julia sets are defined, id., at Chapter 2.8, pp. 138-141. The Mandelbrot set, and methods of generating it by computer iteration, are defined in *The Science of Fractal Images*, by Heinz-Otto Peitgen and Dietmar Saupe, eds., Springer-Verlag, New York, 1988, ISBN 0-387-96608-0 and ISBN 3-540-96608-0, at chapter 4.2.1, pp. 177-179.

Analytical addressing of points mapped to the attractor of an Iterated Function System using the chaos game is described in Peitgen, H.-O.; Jurgens, H.; Saupe, D., *Chaos and Fractals, New Frontiers of Science*, Springer-Verlag, 1992, Chap. 6, p. 297, et seq. See also, Barnsley, M. F., Fractal Modelling of Real World Images, in Peitgen, H.-O; Saupe, D. *The Science of Fractal Images*, Springer-Verlag, New York, 1988.

A notable difference between the Sierpinski and Menger fractal objects, on the one hand, is that they are self-similar by linear contraction mapping, whereas Julia sets and the Mandelbrot set, on the other hand, are self-similar by nonlinear contraction mapping. *Fractals for the Classroom*, Chapter 2.8, p. 141.

Contraction mapping using Iterated Function Systems has been employed for image compression. Barnsley, U.S. Pat. No. 5,065,447. See also Barnsley, Michael F.; Hurd, Lyman P., *Fractal Image Compression*, A K Peters, LTD, Wellesley, Mass., 1993; Barnsley, Michael P., *Fractals Everywhere*, 2nd. Ed., Academic Press Professional, Boston, 1993 (also first ed. 1988). The mathematics of incomplete images, or the addresses of missing pieces, of the mapped fractal are discussed in *Fractals Everywhere*, pp. 122-125, and FIG. IV.100.

It is known that if the numbers employed in the 'chaos game' are not random then incomplete forms of the deterministic fractals will be generated by the 'chaos game' as explained in *Fractals for the Classroom*, Chapters 6.3 and 6.4, pp. 345-364.

Both deterministic and probabilistic Iterated Function Systems can be implemented on neural networks to generate more quickly images of fractal objects. Stark, Jaroslav; "Iterated Function Systems as Neural Networks", Neural Networks, Vol. 4., pp. 679-690, 1991 (received 26 Jan. 1990; revised and accepted 20 Feb. 1991).

SUMMARY OF THE INVENTION

The present invention employs computer-implemented, automated indexing of a stream of signal values which enables segregation of the stream of signal values into patterned subsets according to a new mathematical paradigm. By contrast to other methods currently in use, the present invention enables use of the entire recorded stream of signal values, and does not employ 'filtering' or 'averaging' to pre-process the raw data. It should be kept in mind, however, that some filtering and other data distortions do occur in the process of data collection by the methods of U.S. Pat. No. 5,218,530, in part due to the limitations of the computer hardware which collected the data and in part due to processing methods in the data collection software. An objective of the current invention is to avoid further filtering, averaging, or other 'artifact rejection' beyond that which occurred in the collection and recordation of the raw data. A further objective of the current invention is the preservation of the integrity of the stream of raw signal values so that truly reversible decompositions of the raw stream of signal values remains possible.

The invention is a method of programming and operating a computer:

(1) to map, and thereby to index, a stream of signal values according to addresses on the attractor of an Iterated Function System, which approximates a deterministic fractal such as an affine Sierpinski gasket, (2) to identify one or more patterns in the addresses of the mapped signal values on the attractor, and (3) to automatically segregate signal values into 'bins' by computer-implemented "selection set" algorithms which are employed to confine the patterns identified in the mapped signal values.

BRIEF DESCRIPTION OF DRAWINGS

FIG. 9 appended hereto is a triangular outline representing the outer boundaries of the attractor of an affine Sierpinski gasket with vertices $V_1$, $V_2$, and $V_3$ and Initial Map Point IMP=$MP_0$. FIG. 9 depicts plotted Map Points $MP_1$, $MP_2$, $MP_3$, $MP_4$, $MP_{n-1}$, $MP_n$ and $MP_{n+1}$, which correspond to signal values collected at times $t_1$, $t_2$, $t_3$, $t_4$, $t_{n-1}$, $t_n$ and $t_{n+1}$. It also illustrates the absolute scalar distance ($MP_{n-1}$-$VS_n$) as well as the calculated distances $DIST_n$ and $DIST_{n+1}$ for placing map points $MP_n$ and $MP_{n+1}$ relative to the selected vertex $VS_{n-1}$, $VS_n$, and $VS_{n+1}$. Detectors $D_1$, $D_2$, and $D_3$ are selected from a series of Detectors $D_a$, $D_b$, $D_c$ ... $D_x$. For example, a four-channel system, consisting of four detection electrodes and one reference electrode was used to take the data recorded in disk file "gcm813a" from which a stream of signal values is mapped in the Graphic Images included in this specification. In the hypothetical illustration of FIG. 9, the signal stream from Detector $D_1$ was assigned to Vertex $V_1$, the signal stream from Detector $D_2$ was assigned to Vertex $V_2$, and the signal stream from Detector $D_3$ was assigned to Vertex $V_3$, respectively. For the purposes of the illustration in FIG. 9, the greatest change in hypothetical signal values was detected by Detector $D_1$ for signal values collected at times $t_1$, $t_2$, and $t_3$, so that Vertex $V_1$ was designated as $VS_1$, $VS_2$, and $VS_3$. However, at time $t_4$, the largest signal change was reported by Detector $D_3$, so Vertex $V_3$ was designated as $VS_4$. Similarly, Detector $D_2$ reported the largest change in signal at times $t_{n-1}$, $t_n$, and $t_{n+1}$, so that Vertex $V_2$ was designated as $VS_{n-1}$, $VS_n$, and $V_{n+1}$. FIG. 9 is not to scale but represents a map using contraction factor F=2. Therefore $MP_1$ is one half the distance from IMP to $V_1$, $MP_2$ is half the distance from $MP_1$ to $V_1$, and $MP_3$ is half the distance from $MP_2$ to $V_1$. Then, at time $t_4$ the hypothetical greatest signal change switched from detector $D_1$ to detector $D_3$, so $VS_4$ switched to $V_3$ and $MP_4$ then is plotted at half the distance from $MP_3$ to $V_3$.

FIG. 1 is a schematic diagram of a signal collection system capable of collecting streams of electromagnetic signal values in a form suitable for computerized mapping according to the present invention. Description of Graphic Images. Graphic Images 1-8 are printouts of actual computer displays of the plots of a stream of actual signal values by use of the MS-DOS (Reg. TM) graphics-mode print-screen utility. The Graphic Images display the mapped stream of signal values simultaneously in three different modes in three window sets:

Figure 1:
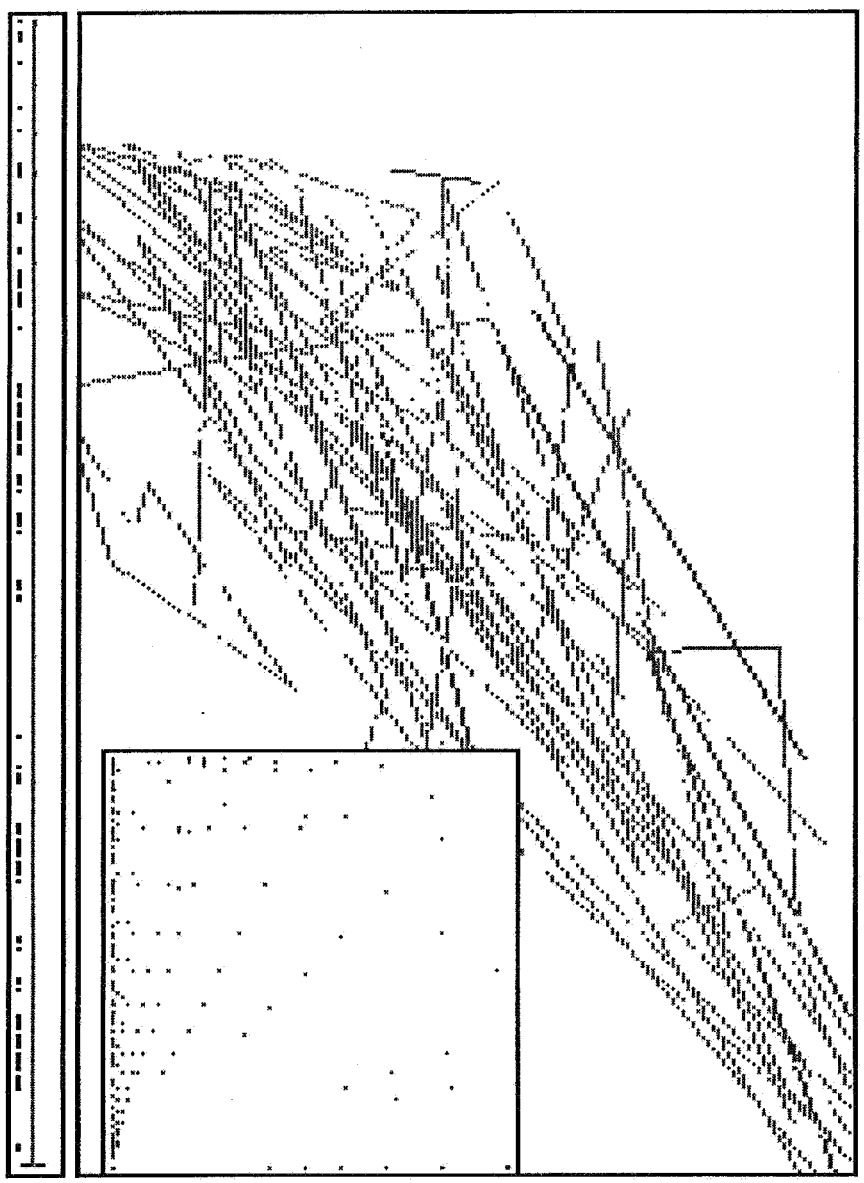
FIGS. 1-8 are printouts of computer screen displays produced during mapping of a stream of signal values according to the invention. They are discussed in detail below.

(1) The lower right window is a phase space portrait according to the methods of U.S. Pat. No. 5,218,530;

(2) The lower left window is the outline of an affine Sierpinski gasket showing signal values contraction-mapped according to the method of the present invention; and (3) The bar window at the top displays the signal values plotted on two or more time lines according to the collection sequence. In Graphic Images 1-6, which were created with program fsa2a.exe, the upper time bar displays the signal values confined within the rectangular selection set, and the lower time bar displays signal values confined within the wedge selection set.

Graphic Image 1 is a display of the entire selected stream of signal values taken at 250 discrete times in the time series $t_n$ from disk file "gcm813a", displayed in both the fractal mapping window on the lower left and the phase space portrait window on the lower right, with the time bar window at the top. No selection sets are active in Graphic Image 1.

Graphic Image 2 is a graphic print-screen which depicts both the 'rectangular selection set' and the 'wedge selection set' within the lower left window. The reference at the lower left margin immediately below the window is "R\< >", indicating by the "< >" that the phase space portrait depicted in the lower right window is displaying the same mapped signal values as are confined within the wedge selection set on the Sierpinski gasket depicted in the lower left window. Note that the wedge selection set has confined a single "ray" of mapped signal values. The "ray" of signal values is focused upon the upper left vertex of the affine Sierpinski gasket. Note that the hypotenuse of the affine, right Sierpinski gasket bulges outwardly in Graphic Image 1. This deformation of the hypotenuse is due to use of a contraction mapping factor F<2, in this case F=1.2. The use of a factor F<2 sometimes makes the ray patterns in mapped signal values appear more clearly. If the factor F were 2 then the hypotenuse would closely conform to a straight line.

Graphic Image 3 shows the identical positioning of the wedge and rectangular selection sets as in Graphic Image 2, except that the screen display has been toggled with the F5 function key to display the phase space portrait in the lower right window of the mapped signal values confined with the rectangular selection set, rather than the wedge selection set. This is indicated by the "[ ]" reference appearing at the lower left margin in Graphic Image 3.

Graphic Image 3 displays in the phase space portrait window the result of activating the rectangular selection set. The subset of signal values corresponding to the pattern confined within the rectangular selection set is displayed in all three modes, segregated from the remainder of the plotted signal values. Note that the segregated subset of signal values corresponding to a single "ray" forms a compact block in the time-bar window at the top of the Graphic Image. The multi-window display format in the Graphic Images illustrates that a patterned subset of signal values segregated according to the present invention is readily available for cross-analysis in other modes.

Graphic Image 4 illustrates, by comparison with Graphic Image 1, the result when scalp electrode assignments to vertices are altered as follows: $D_2=V_1$, $D_3=V_2$, $D_4=V_3$, using the same raw data file "gcm813a". Thus, it is apparent that the selection of the electrode triads to be displayed is significant. No selection set is active in Graphic Image 4. Note that when making the electrode assignments upon initiation of the computer program it is necessary only to indicate the detector numeral, not including the character "D".

Graphic Image 5 depicts a rectangular selection set positioned to confine two "columns" of signal values which appear approximately perpendicular to one side of the Sierpinski gasket, and simultaneously displays the confined "columns" of mapped signal values in the phase space portrait also. Note that the vector alignments in the phase space portrait are similar, but not identical. For this reason, it would be difficult to describe the similarities by an algorithm which would select these vectors directly from the phase space portrait. This illustrates how the selection sets of the present invention can isolate a pattern which is non-random, but not necessarily precise. Several of the Graphic Images show that several rays of mapped signal values can similarly align to form columns or rows of mapped signal values approximately perpendicular to the sides of the Sierpinski gasket. These columns or rows readily can be confined by a rectangular selection set. These columns or rows of mapped signal values roughly align across several similarly-aligned rays. When the columns or rows are segregated and displayed in the phase space portrait format they also are seen to share remarkably similar alignments in the phase space portrait, but not with sufficient precision that those similar alignments could be readily defined with mathematical precision to segregate the pattern by any methods known to the inventors other than the present invention. Note that these column and row patterns in the mapping to the Sierpinski gasket are formed by temporally-discontinuous subsets of signal values when displayed in the time bar window. They thus would be relatively difficult to isolate with the 'wave' paradigms such as the Fast Fourier Transform.

Graphic Image 6 depicts confinement of more complex patterns which appear to display scaled, self-similarity on the Sierpinski gasket. It also depicts the selected subset of signal values in the phase space portrait. Note the relatively compact nature of the resulting image in the phase space portrait.

Graphic Image 7 depicts a 'fan' of wedge selection sets which subdivides the entire Sierpinski gasket and thus automatically segregates the entire set of signal values within the swath into bins without visual identification or manual positioning of the selection sets. The wedges in the fan are used to set "windows" for the phase space portraits, one window for each wedge selection set in the fan. This 'fan' selection set is only partially implemented in the computer program fsa4.bas appended hereto as Appendix 2 and additional amending code is necessary to fully implement a 'fan' selection set. The fan can be manually adjusted to cover only a portion of the Sierpinski gasket. The ">" character at the left margin of the time bars indicates which time bar corresponds to the active selection set in the phase space portraits.

Graphic Image 8 displays an image created by mapping a stream of raw signal values when an electronically generated sine wave was imposed upon the signal detection electrodes. The precision of the sine wave is unknown. This image illustrates that signal values recorded from a source other than the human scalp can be displayed and analyzed by the current invention.

Screen Display References and Program Operation Keys

The printed references at the bottom of the Graphic Images 1-6 are interpreted as follows: "gcm813a" is the name of a computer disk file. This file name was manually specified in response to the prompt when the F6 function key was pressed at the initiation of the program. The disk file records streams of signal values collected by use of four channels (or "detectors D") according to the data collection methods of U.S. Pat. No. 5,218,530. The numeral "2" identifies the 'correction factor' employed in depicting the phase space portrait, which in this case is the "tree" version plotted from an origin fixed at the center of the window, as distinguished from the "box" version which would be plotted from an origin fixed at a corner of the window and would be indicated by numeral "11". The numeral "250" is the number of discrete time intervals at which the signal values mapped to the display were recorded, that is, in Graphic Images 1-4 $t_{max}=250$ in the time series $t_n=t_1, t_2, \ldots t_{max}$. The numeral "1250" corresponds to the number of discrete sets of signal values read from the disk file "gcm813a" and mapped in the display. It is the number which was entered manually in response to the prompt "Number of points" upon initiation of the computer program fsa2a.bas which is Appendix 1 hereto. The symbols "R\< >" or "L\[ ]" appearing at the left margin below the windows reflect a toggle function manually operated with the F5 keyboard function key in the software programming. By use of the F5 keyboard function key, this parameter toggles between "upper Right" and "lower Left", respectively. This F5 toggle key interacts with other keyboard function keys [F1, F2, F7, F8, F9 and F10] to manually position selection sets. F1 and F2 control the left and right angular movements, respectively, of the two rays which form the wedge selection set. The F7, F8, F9, and F10 function keys manually control up, left, right and down movements, respectively, of the upper left and lower right corners of the rectangular selection set. Thus, it takes a combination of toggles on the F5 function key, plus use of the F1 and F2 function keys to manually position the wedge selection set. It takes a combination of toggles on the F5 function key, plus the F7, F8, F9, and F10 function keys to manually position the rectangular selection set.

The F5 function key also toggles between the "< >" and the "[ ]" symbols, which indicate whether the phase space portrait is displaying the subset of signal values segregated by the 'wedge' selection set or the subset segregated by the 'rectangular' selection set. Although not showed in the reference line, the Sierpinski gasket in Graphic Images 1-6 is formed using a contraction mapping factor F=1.2, and selecting scalp electrode assignments to vertices on the Sierpinski gasket as follows: $D_1=V_1, D_2=V_2, D_3=V_3$, using raw data file "gcm813a".

The graphic display illustrated by Graphic Image 7 shows a modified time bar window at the top to graphically illustrate on the time bar which section of the fan covers the mapped signal values at a given point on the time line.

DESCRIPTION OF THE PREFERRED EMBODIMENT

One species of the invention enables automatic, computer-assisted selection of subsets of signal values which appear as linear rays pointing at a vertex of an affine Sierpinski gasket onto which the signal values have been contraction mapped by the 'chaos game'. The Sierpinski gasket is affine because a right triangle, rather than an equilateral triangle, is used for convenience in addressing the display on the computer screen. The gasket is further distorted when the contraction mapping factor F is less than 2. This distortion often is useful to display patterns more clearly for identification and confinement. Signal values corresponding to particular linear rays can be manually selected into bins using a 'selection set' manipulated by keyboard function and arrow keys. It can automatically be determined whether more than one 'event' has fallen into the same wedge selection set. This temporal segregation within a selection subset is readily visualized in Graphic Images in which mapped signal values within a single wedge on the affine Sierpinski gasket are seen to be grouped into separate time blocks along the time line in the time-bar window. It often is easy to manipulate the selection sets to further segregate the subset of signal values into sub-subsets of temporally-continuous signal values.

The number F, or 'contraction mapping factor', is the parameter which controls the rate of contraction in the contraction mapping by the Iterated Function System. F can be adjusted to any number greater than unity. If F is equal to unity no contraction will occur. If F is less than unity expansion will occur and the display can become effectively unconfined.

The current embodiment of the invention employs the 'chaos game' to contraction map to an affine Sierpinski gasket using contraction factor F>1 by the following steps:

(1) defining a Triangle TRI having vertices $V_1, V_2$ and $V_3$, to each of which is assigned one of three signal Detectors, $D_1, D_2$ and $D_3$, selected from the series of signal Detectors $D_a, D_b, D_c, \ldots D_x$;

(2) selecting streams of serial signal values $S_nD_1, S_nD_2, S_nD_3$, collected substantially simultaneously at discrete serial collection times $t_n$ for $n=1, 2, 3 \ldots n$, from signal Detectors $D_1, D_2$ and $D_3$;

(3) defining initial signal values, which for convenience may be initialized to zero, $[S_0D_1=0, S_0D_2=0, S_0D_3=0]$;

(4) selecting a maximum number MAX of discrete serial signal value collection times $[t_n = t_{max}]$;

(5) selecting an initial Map Point [IMP] at the center of the Triangle TRI corresponding to time $t_0$ within the time series $t_n$, which Initial Map Point is defined to be $MP_0$ within the series $MP_n$, for n=0, 1, 2, 3, . . . n;

(6) Iterating for n=1, 2, 3, . . . MAX, the following steps:

6(A) calculating the absolute scalar [ABS] change [Delta $S_n D_1$, Delta $S_n D_2$, and Delta $S_n D_3$] between successive signal values collected at serial Times $[t_{n-1}$ and $t_n]$ from each of said three signal detectors $[D_1, D_2,$ and $D_3]$, said scalar change calculated as: [Delta $S_n D_1$=ABS $(S_n D_1 - S_n D_1)$; Delta $S_n D_2$=ABS $(S_n D_2 - S_{n-1} D_2)$; Delta $S_n D_3$=ABS $(S_n D_3 - S_{n-1} D_3)$ ];

6(B) selecting a vertex $VS_n$ from among the three vertices $[V_1, V_2,$ or $V_3]$ on the Sierpinski gasket to which has been assigned that signal detector $[D_1, D_2,$ or $D_3]$ which produced the largest scalar change [Delta $S_n D_1$, Delta $S_n D_2$, or Delta $S_n D_3$] at $t_n$;

6(C) plotting a serial Map Point $[MP_n]$ on a line between the previous map point $MP_{n-1}$ and the vertex $VS_n$, at a distance $DIST_n$ from the prior Mapped Point $[MP_{n-1}]$ toward said vertex $VS_n$, said distance $DIST_n$ calculated as the quotient of the absolute scalar [ABS] linear distance between the prior Mapped Point $[MP_{n-1}]$ and the selected vertex $VS_n$, divided by the Contraction Mapping Factor F: $[DIST_n = ABS(MP_{n-1} - VS_n)/F]$; and 6(D) incrementing n by 1 and returning to step 6(A) until n=MAX.

Figure 9:
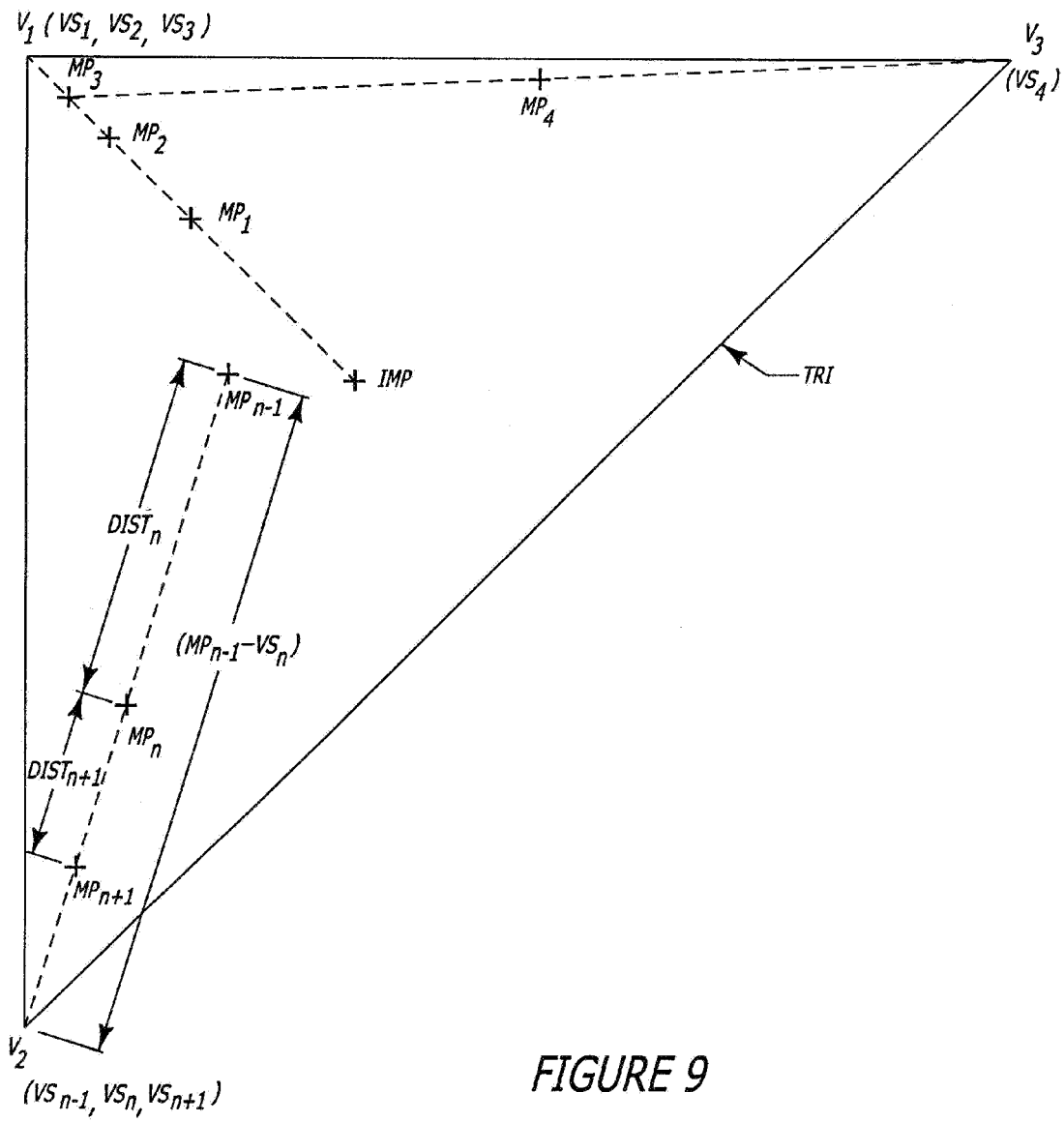
FIG. 9 is a schematic diagram which illustrates in principle a geometry which can be employed in mapping parsed electronic data to a Sierpinsky gasket form of fractal.
Figure 10:
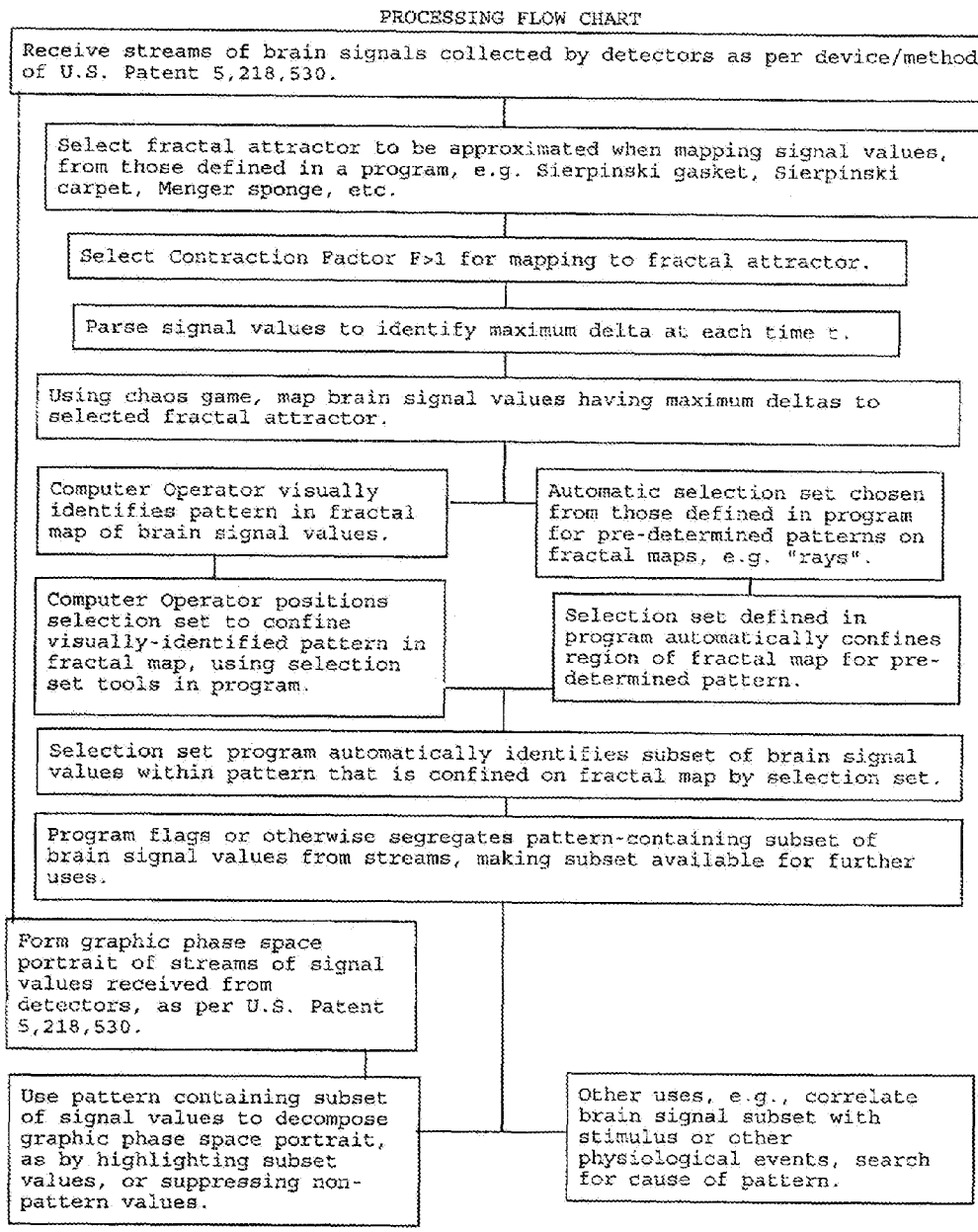
FIG. 10 is a PROCESSING FLOW CHART which illustrates one possible sequence of steps to implement the invention.
Figure 11:
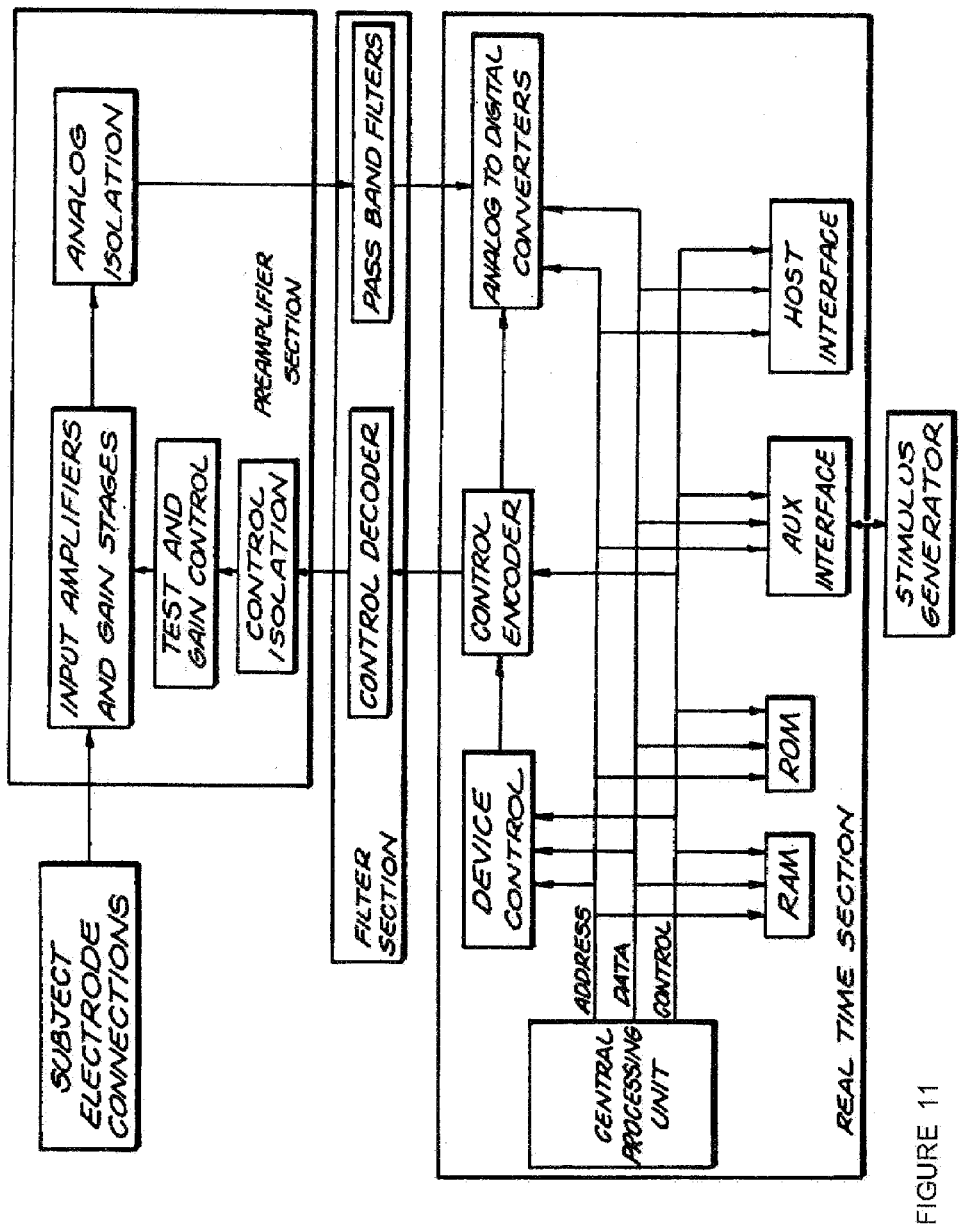
FIG. 11 is a schematic diagram, reproduced and renumbered from the inventors' U.S. Pat. No. 5,218,530, which illustrates a signal collection system capable of collecting streams of electromagnetic signal values in a form suitable for computerized mapping according to the present invention.

The schematic in FIG. 9 and the PROCESSING FLOW CHART in FIG. 10 illustrate one sequence of the foregoing steps in the embodiment preferred at the date of filing of the application. In principle, the sequential order of the steps depicted in the PROCESSING FLOW CHART could be altered to some extent without materially affecting the results. For example, selection of the fractal attractor, Contraction Factor, and an automatic selection set could, in principle, be made in any order before or after receiving the streams of brain signals and before or after parsing the streams of brain signals.

The order of steps recited above is not invariant and the order in the computer programs in Appendix 1 and Appendix 2 varies from the foregoing order of steps.

For a stream of electromagnetic signal values collected substantially simultaneously at discrete serial times from electrodes on the scalp of a human subject, by the methods disclosed in U.S. Pat. No. 5,218,530, the preferred contraction factor F is a constant within the range $2 \_>F>1$. For certain simple patterns the contraction factor is preferred in the more narrow range $1.7>F>1.15$. Prominent, relatively simple patterns emerge as a result of mapping signal values collected by the methods and devices of U.S. Pat. No. 5,218,530 when F is within these ranges. The appearance of these prominent, simple patterns renders it feasible to automatically segregate much of the signal stream into distinct 'bins'. In particular, the contraction factor F can be adjusted so that portions of the signal stream when mapped to an affine Sierpinski gasket appear as linear rays pointing towards a vertex of the gasket, as in Graphic Images 1-3. The mapped signal values which correspond to such a linear ray can be automatically identified and segregated into a separate 'bin' by computer-implemented algorithms.

The 'selection set' as presently implemented can be (i) an adjustable 'rectangle selection set' or (ii) an adjustable 'wedge selection set', or (iii) a plurality of wedge selection sets.

The rectangle selection set is positioned by adjusting diagonal corners of a rectangular 'window' with keyboard function keys to exclusively encompass a visually detected pattern in the map. The exclusion is not necessarily perfect, but perfection often is not necessary. Then the subset of mapped signal values falling within the rectangular selection window automatically is segregated by the computer from the stream of signal values. Improved selection within the segregated subset can be obtained by setting aside temporally discontinuous signal values, or temporally-distant signal values.

One species of the 'wedge selection set' is bounded by two rays, whose common focal point is a vertex of the Sierpinski gasket, and an adjustable arc which closes the outer boundary, effectively forming a pie-shaped wedge. The angle of each of the two boundary rays, expressed in radians, is adjustable. That is, radial distance from the vertex to the defining arc and the radial angles of the two defining rays can be selected manually.

In a second species of the 'wedge selection set', the common focal point of the two defining rays of the wedge is the upper left corner of the rectangular selection set. In this species, the radial distance from the focal point of the wedge to the outer arc is identical with the diagonal of the rectangular selection set. Thus, this species of wedge selection set moves about with, and confines a sub-set which substantially but not entirely overlaps the rectangular selection set, the rectangular selection set.

Alternatively, the signal values in a stream can be segregated automatically by the computer into pre-programmed selection sets or 'bins'. For example, Graphic Image 7 illustrates that portions or all of the Sierpinski gasket can be subdivided by a 'fan' of wedge selection sets, all having the identical vertex of the Sierpinski gasket as a focal point. In this manner each and every mapped signal value is segregated into a bin corresponding to one of the wedges in the fan. The effect of the 'fan' is to automatically 'recognize' and segregate all rays of mapped signal values which fall within the 'fan'. The number of radians in the defining arc of each successive wedge selection set within a fan of wedge selection sets can be progressively contracted beginning with the largest wedge(s) in the center of the fan and contracting successive wedges as the two boundary rays which define the outer limits of the fan are approached. Progressive contraction of wedges can be done according to logarithmic powers of the contraction mapping factor F, starting with power zero for the greatest wedge(s) centered on, or adjacent to, the bisector of the angle of the Sierpinski gasket which is the focal point of the defining boundary rays of the wedge selection set. The number of radians in the defining arcs of successive wedges contracts exponentially as the wedge positions progressively depart from said bisector and approach either side of the Sierpinski gasket. A fan thus can be so constructed to more closely conform to the inherently contractive pattern of the mapping process. Note that in this exponentially-defined fan of wedges, the smaller the contraction factor F, the narrower and more discriminating are the wedges in the fan.

The detail of patterns on the Sierpinski gasket can be inspected by increasing the zoom in the display window. The depth of the detail of the deterministic fractal is infinite, in principle, but in practice the detail of the mapped signal values is limited by the resolution of the signal values, the resolution of the computer devices and buffers, and the number of discrete signal values mapped to the gasket.

The arbitrary Initial Map Point $[IMP=MP_0]$ for the start of the mapping may be made less arbitrary, and the mapping more efficient, by trial and error. The Initial Map Point IMP can be arbitrarily near or within the deterministic fractal. For convenience in the current implementation the Initial Map Point IMP is placed at the calculated center of the Sierpinski gasket, that is, at the intersection of imaginary rays bisecting two of the three angles of the gasket.

The contraction mapping of the present invention is implemented for interactive use with the display of signal values in the phase space diagram of U.S. Pat. No. 5,218, 530. For example, the segregated subset of signal values which contribute to an apparent pattern on the deterministic fractal in the present invention is displayed simultaneously in the phase space portrait. Thus, the present invention enables decomposition of phase space portraits.

OBJECTIVES, FEATURES, AND USES OF THE INVENTION

The subsets of signal values segregated by the method of the present invention have several distinct types of uses.

First, apparently random signal values can, to a large extent, though not completely, be segregated from patterned (i.e. non-random) signal values. In prior practice this would be viewed as suppression of "noise". However, the inventors view the apparently random signal values simply as uncharacterized data, rather than as "noise". This is because such uncharacterized signal values might be shown to be meaningful by other methods. For example, such apparently random data might be indicative of a transition to a chaotic regime, or indicative of transition from one dynamic pattern to another dynamic pattern. This use of the method can give a visual sense of what other types of analysis call the 'signal-to-noise' ratio.

Second, there often are sub-patterns apparent in the contraction mapping which are separable from each other, from which it may be postulated that segregation of the signal values for the respective sub-patterns will tend to decompose the stream of signal values into separate 'events'.

Third, one or more individual subsets can be further analyzed to find algorithms which more precisely correspond to the attractor of such segregated subsets of signal values. This is useful as a tool to search for more precise algorithms to be used in automatic computer 'recognition' of patterns.

Fourth, certain repetitive patterns in the contraction mappings lend themselves to segregation by simple, computer-implemented algorithms, and thus support automatic 'recognition' by computer without need for intervening visual identification and manual segregation.

Fifth, investigators can experiment for the purpose of empirically correlating extracted subsets of patterned signal values with stimuli or physiologic function, even though no algorithm to precisely generate that subset of signal values is known. That is, once a subset of signal values results in a pattern in the mapping to the deterministic fractal it may be postulated that a non-random process probably caused that pattern. Upon segregation of the subset of signal values which correspond to that pattern it becomes more feasible to search for the cause of the pattern. In effect, the pattern-segregation method narrows the parameters of the investigation. The method does not show why there is a pattern. Rather it is a tool for use in identifying and isolating the signal values which contribute to a pattern to aid in searching for the cause of the pattern.

For example, apparent patterns within a phase space portrait could be confined and segregated with a selection set such as is implemented in U.S. Pat. No. 5,218,530, and the signal values so selected then could be simultaneously displayed as mapped to a deterministic fractal to see if patterns suspected in the phase space portrait appear when mapped to the fractal.

For a more intuitive understanding of the uses of the method disclosed herein, it may postulated that least one attractor probably underlies any visible "pattern" on the deterministic fractal. It further may be postulated that the attractor(s) underlying a pattern probably inhere in, and thus express, some physical or biological function. That is, if there is a pattern then it may be postulated that a physical or biological function probably is producing that pattern. It then is postulated that if the signal values which contribute to a pattern can be identified and isolated, then that isolated subset of signal values may be empirically related to the causal physical or biological event. This empirical correlation between the segregated subset of pattern-producing signal values can be postulated, even though the exact algorithm which precisely generates that segregated subset of signal values is unknown—or, more precisely, the algorithm which generates the attractor to which that subset of signal values is attracted is unknown. Thus, the ability to decompose the raw stream of signal values into pattern-containing subsets, enables practical, empirical testing of the postulate that there is a causal physical or biological process which is reflected in that segregated subset. These segregated subsets of pattern-containing signal values cannot be obtained by other methods known to the inventors.

More sophisticated postulates also may be useful. If non-randomness, that is, a pattern, appears when the stream of signal values is mapped to the attractor of a deterministic fractal such as the Sierpinski gasket or Sierpinski carpet, then one may postulate that the pattern in the mapped signal probably can be described topologically by a compact, one-dimensional, linear algorithm which describes the addresses of the deterministic fractal onto which the mapped signal values have fallen. Similarly, if a pattern emerges when the stream of signal values is mapped to the Mandelbrot Set, one may postulate that the mapped pattern probably can be described topologically by a nonlinear algorithm forming a Julia set.

The foregoing postulates are not essential to make or use the invention, but they may aid in developing a more intuitive sense of its uses. The Graphic Images included with this specification should be reviewed with the foregoing postulates in mind.

An objective of the invention is to exploit the concept that the attractors of complex deterministic fractals, such as the Sierpinski gasket and the Mandelbrot Set, inherently index subclasses of less-complex attractors. The computer-implemented algorithms which confine or encompass the patterns of addresses of signal values mapped to a deterministic fractal, according to the method of the present invention, thus might loosely be thought of as confining a limited subclass of unknown attractors from within the deterministic fractal to which the signal values have been mapped.

Humans can readily perceive "patterns" without any knowledge whatever of a mathematical description of the perceived "pattern". An objective of the present invention is to implement the concept that a "pattern" perceived in a mapping of signal values to a deterministic fractal can be confined or encompassed by a simple, relatively arbitrary, computer-implemented "selection set", and then algorithms to automatically segregate the signal values which contribute to the "pattern" can be implemented—all without knowing a precise mathematical algorithm to exactly generate the attractor of those signal values. Therefore, by use of the method, the signal values which contribute to an identified pattern can be segregated automatically by computer to a separate subset or 'bin' based upon patterns displayed by the mapped signal values. Further, after some experience with the method, it is apparent that certain patterns in the mapped signal values can be confined by predetermined selection sets, and then automatically segregated, without visual identification and manual selection. That is, once a pattern has been identified and defined by an appropriate selection set, the computer can be programmed to automatically "recognize" and segregate such patterns without manual intervention. Thus, the method of the present invention can be employed to develop new selection sets which thereafter will automatically 'decompose' portions of a complex raw stream of signal values into segregated subsets according to previously-defined patterns, without manual intervention.

More complex patterns displaying scaled self-similarity also can be segregated with the selection sets as illustrated in the Graphic Images. These complex, scaled, self-similar patterns from the mapping to the Sierpinski gasket also show remarkable confinement when displayed in the phase space portrait. No other method of extracting such subsets from the phase space portraits is known to the inventors.

Conceptions not Implemented in Current Computer Programs

In principle, the contraction mapping factor F does not have to be a constant, provided that the function controlling the parameter F causes contraction in the mapping process and does not itself produce random numbers. Complex functions for F, however, may render the resulting map uninterpretable. The inventors conceive that non-linearity can be obtained in the contraction mapping process, to search for non-linear patterns, by defining the contraction mapping factor F as the variable result of a function. Of course, contraction factors greater than 2 also can be used.

The mapping process inherently assigns an address on the deterministic fractal to each mapped triad of signal values which was simultaneously collected at each discrete time $t_n$ which is mapped. More precise selection sets could be implemented, based upon the coding of addresses on deterministic fractals, because each signal value can be assigned an address on the deterministic fractal. For example, a third species of 'triangular' selection set could be implemented with respect to the Sierpinski gasket. The gasket could be subdivided into three selection-set triangles by drawing lines from each of the three vertices $V_1$, $V_2$, and $V_3$ to the Initial Map Point IMP located, for this purpose, at the center of the Sierpinski gasket. Each of the resulting selection-set triangles could in turn be similarly subdivided into sub-subtriangles, and so forth. Of course, display windows in the phase space portrait could display the selected subsets of mapped signal values for any one or any combination of the selection set triangles. In principle, the displayed map could be zoomed to any desired degree of magnification, and the triangular selection-sets subdivided to any desired degree, and then a pointing device such as a computer mouse could be used to select particular triangular selection sub-sets for display in the phase space portrait.

A selection set system could employ a computer mouse, track ball or other pointer device in the manner implemented in many commercial computer-aided design ("CAD") programs.

The method of programming described herein could be wholly or partially built into computer-hardware, such as a chip or a board which is hard-wired to perform the iterative processes. Alternatively, the method could be implemented as a neural network either in hardware or in software. The hardware chip could, for example, employ the fan selection set of the invention in hardwired printed circuits. Alternatively, some or all of the process could be in ROM (read-only memory), PROM (programmable, read-only memory) or EPROM (erasable, programmable, read-only memory) hardware. Of course, certain human processes, such as visual inspection for patterns and manual manipulation-of selection sets to confine patterns, could not be built into hardware. However, automatic 'recognition' of previously-defined selection sets, to recover particular previously-recognized patterns, could be built into hardware.

It should be noted that the automatic 'recognition' and confinement of patterns in mapped signal values would not necessarily require that the patterns be visually displayed. Visual display is necessary only when visual inspection and/or manual confinement of patterns is desired. For example, the 'fan' of wedge selection sets could be accompanied by separate windows to display the signal points confined by each separate wedge selection set. This could be completely automatic, with no visual identification or manual selection whatever, based upon the pre-defined fan of wedge selection sets.

The present implementation of the method employs only an affine Sierpinski gasket deterministic fractal as an attractor. However, Iterated Function Systems for generation of other deterministic or probabilistic fractals are known which could be adapted to map signal values to the attractors of such other deterministic fractals. Such other fractals include the Sierpinski carpet, the Menger Sponge, and the Mandelbrot Set. The inventors conceive that Iterated Function Systems to map signal values to approximated fractal attractors could be implemented in polar and spherical coordinates by defining the radius of the polar or spherical coordinate system equivalently to a Cantor Set. Increased dimensions of 'fractality' could be injected by defining polar and spherical angles analogously to a Cantor Set. The inventors conceive that it would be feasible to transform a stream of raw signal values with a Fast Fourier Transform and display the resulting wave forms in one or more other windows, highlighting by colors those portions of the wave forms which correspond in the time domain to mapped signal values confined within a selection set according to the present invention.

Syntax Conventions

The following conventions are employed in the syntax of the claims:

"Signal detectors" are assigned the capital letter "D", followed by a numeral indicating a particular detector in the sequence, such as, $D_1$, $D_2$ and $D_3$.

"Discrete times" are indicated by lower case "t" followed by a numeral indicating the particular place in the time sequence, such as, $t_1$, $t_2$, and $t_3$. Signal values are assigned a capital letter "S" followed by a numeral indicating the time the signal was taken. For example signal $S_1$ was collected at time $t_1$. Signal values may further be assigned a letter and number to indicate the particular detector from which the signal was collected, such as, $S_1D_1$, meaning the signal value collected from detector $D_1$ at time $t_1$.

A "series" of indeterminate length is indicated by listing the first few members of the series followed by four periods and the letter "n". An example is the time series "$t_1$, $t_2$, $t_3$, . . . $t_n$." Another example is the signal detector series "$D_1$, $D_2$, $D_3$, . . . $D_n$." The length of the series is user determined.

In the phase space portraits drawing "point entities" are referred to by the capital letter "P" followed by a numeral indicating the time at which the signal data establishing the coordinates of the point was collected. Thus, point "$P_1$" is defined by the signal data collected at time $t_1$. The three coordinates of a point are defined by signal data collected substantially simultaneously from three different detectors. For example, "x" could be the signal data from detector $D_1$, "y" the signal data from detector $D_2$, and "z" the signal data from detector $D_3$.

In the phase space portraits drawing "line entities" are referred to by the capital letters "LI" followed by a numeral indicating the time of the first point entity, such as "$LI_1$" referring to the line connecting points $P_1$ and $P_2$, which starts at time $t_1$ and extends to time $t_2$. "$LI_2$" refers to the line connecting points $P_2$ and $P_3$, starting at time $t_2$.

In the phase space portraits drawing "layers" are referred to by the capital letters "LA" followed by a numeral indicating place in the sequence of a series of layers, such as $LA_1$, $LA_2$, and $LA_3$. Point entities drawn on different layers are designated by a capital "P" followed by a numeral designating time, by the capital letters "LA" and a numeral indicate which layer in the sequence. For example, "$P_1LA_2$" means Point 1 on Layer 2, whose coordinates are defined by signal data taken at time $t_1$, from the unique subset 2 of detectors whose signal data is employed to define the points on Layer 2.

"Color-time" sequences employ the syntax capital "C" followed by a numeral for a distinctive color, followed by lower case "t" followed by a numeral for a discrete time. Thus, "$C_1t_1$" means the color 1 is assigned to time $t_1$ in a pre-determined table. Where colors are employed to visually illustrate a time sequence, the sequence of colors is pre-determined in a table.

Figure 2:
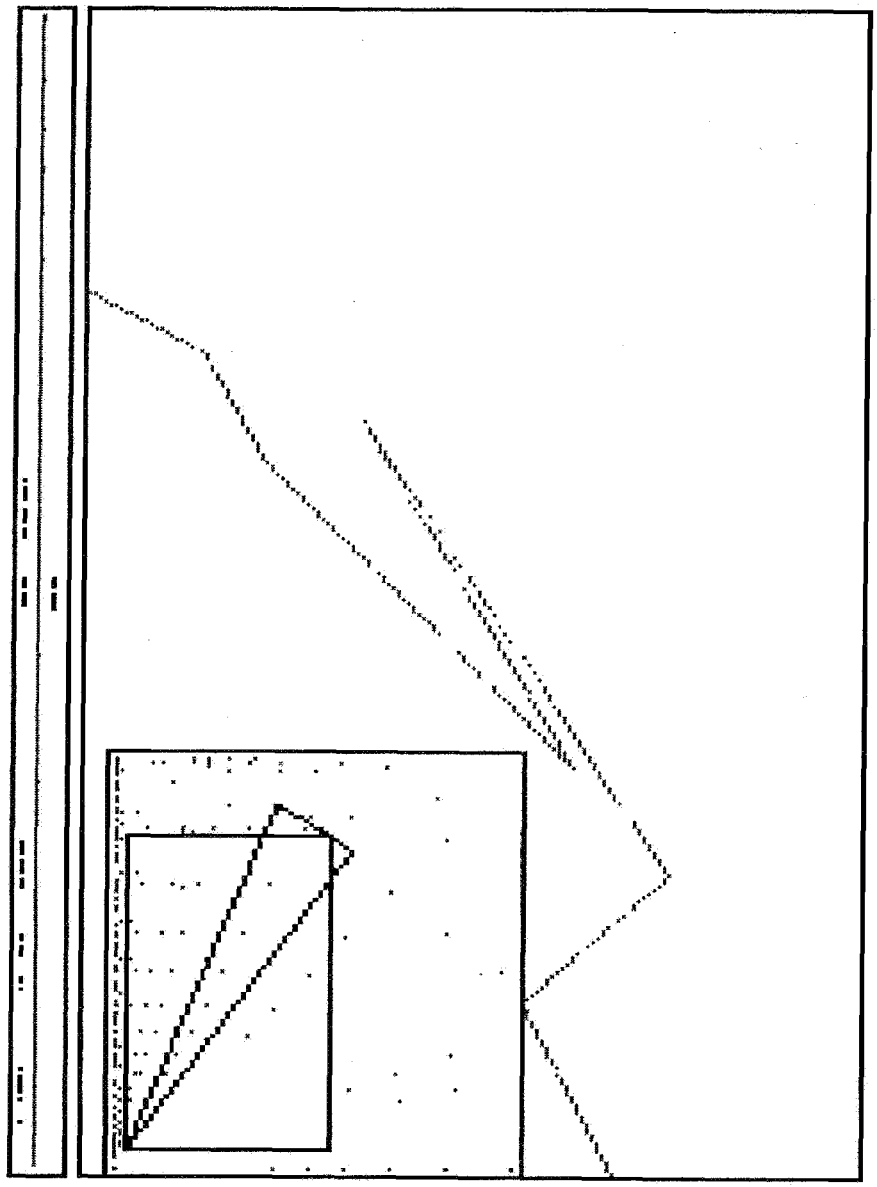
Figure 3:
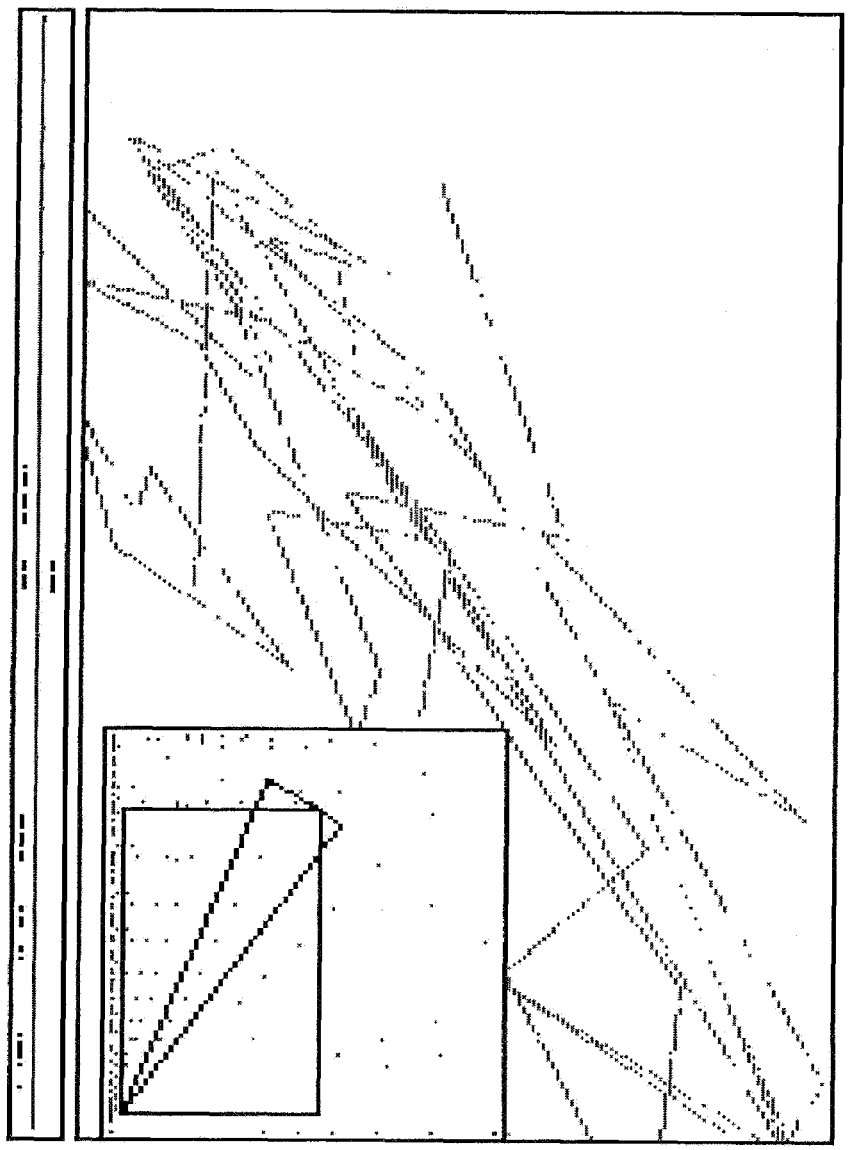
Figure 4:
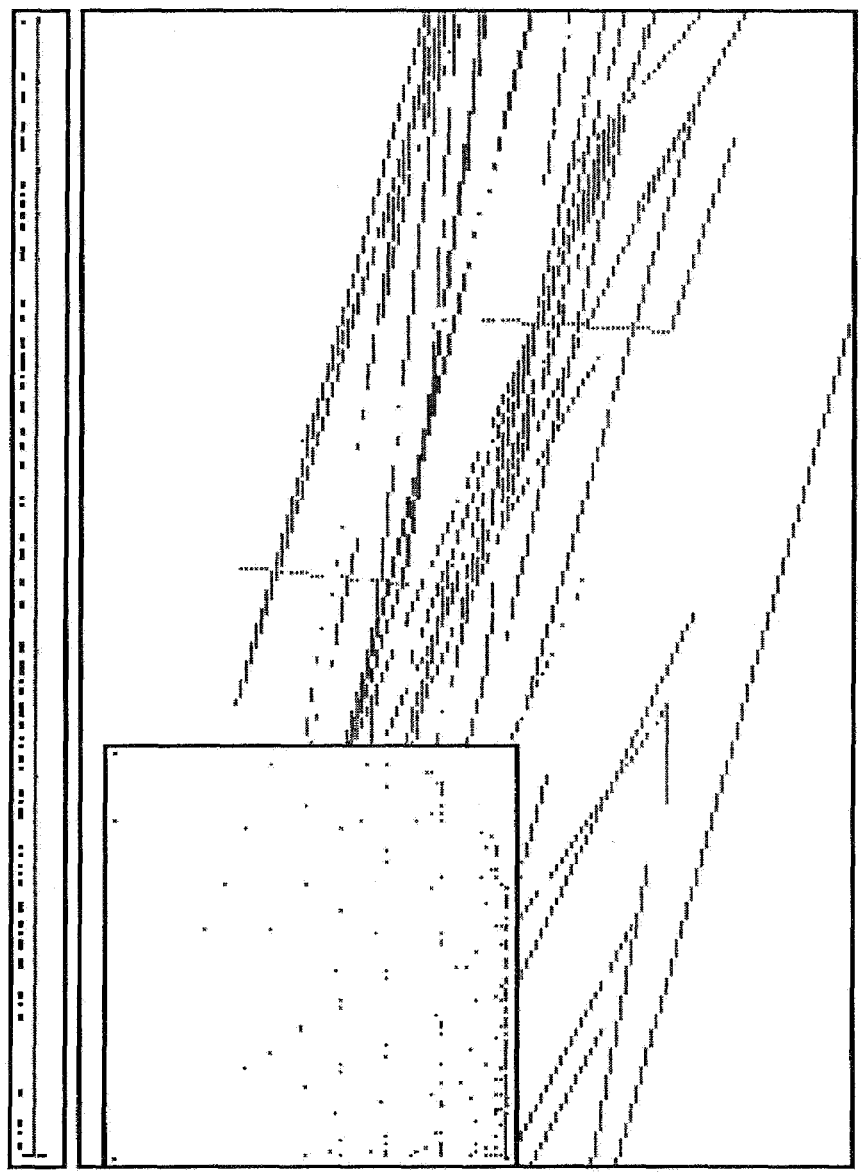
Figure 5:
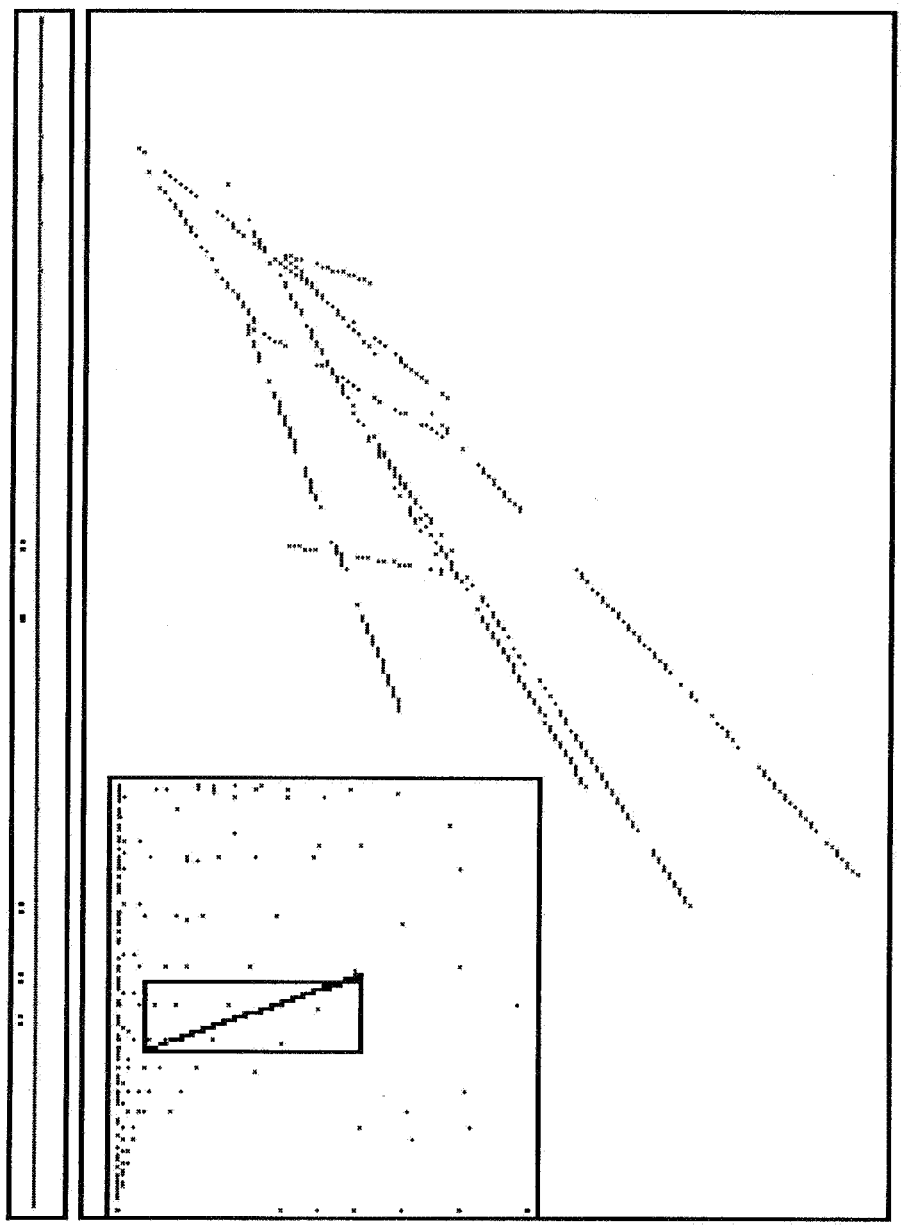
Figure 6:
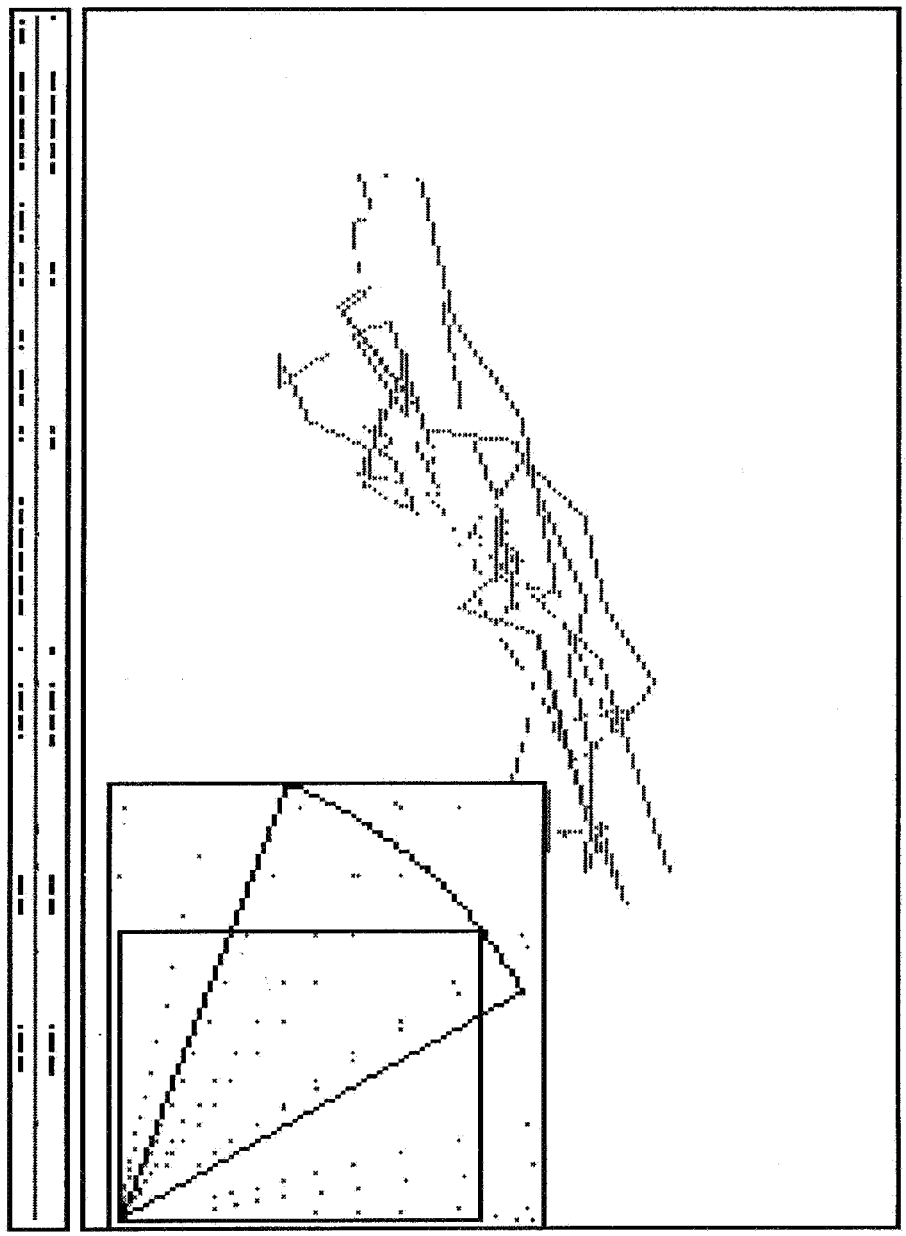
Figure 7:
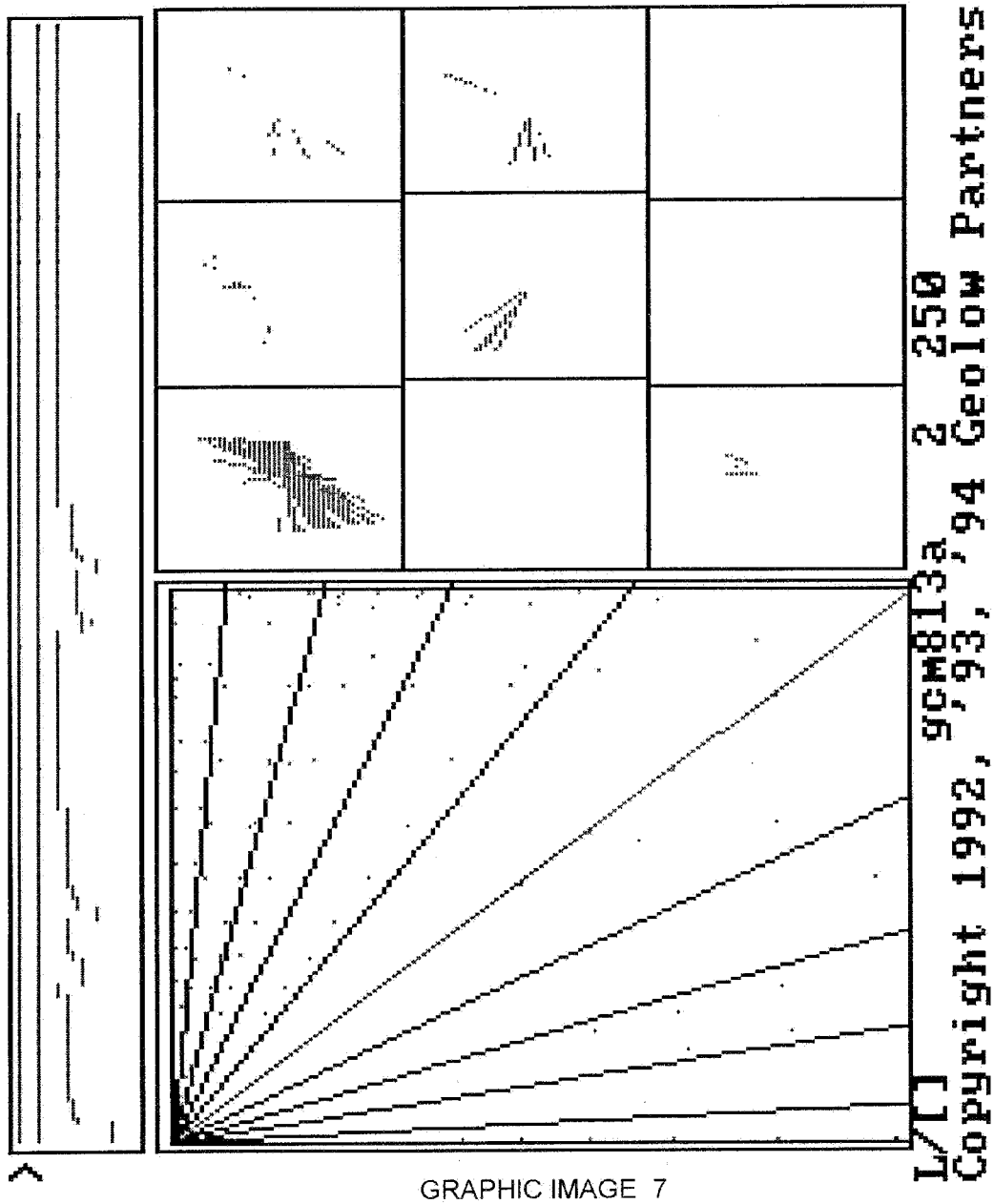
Figure 8:
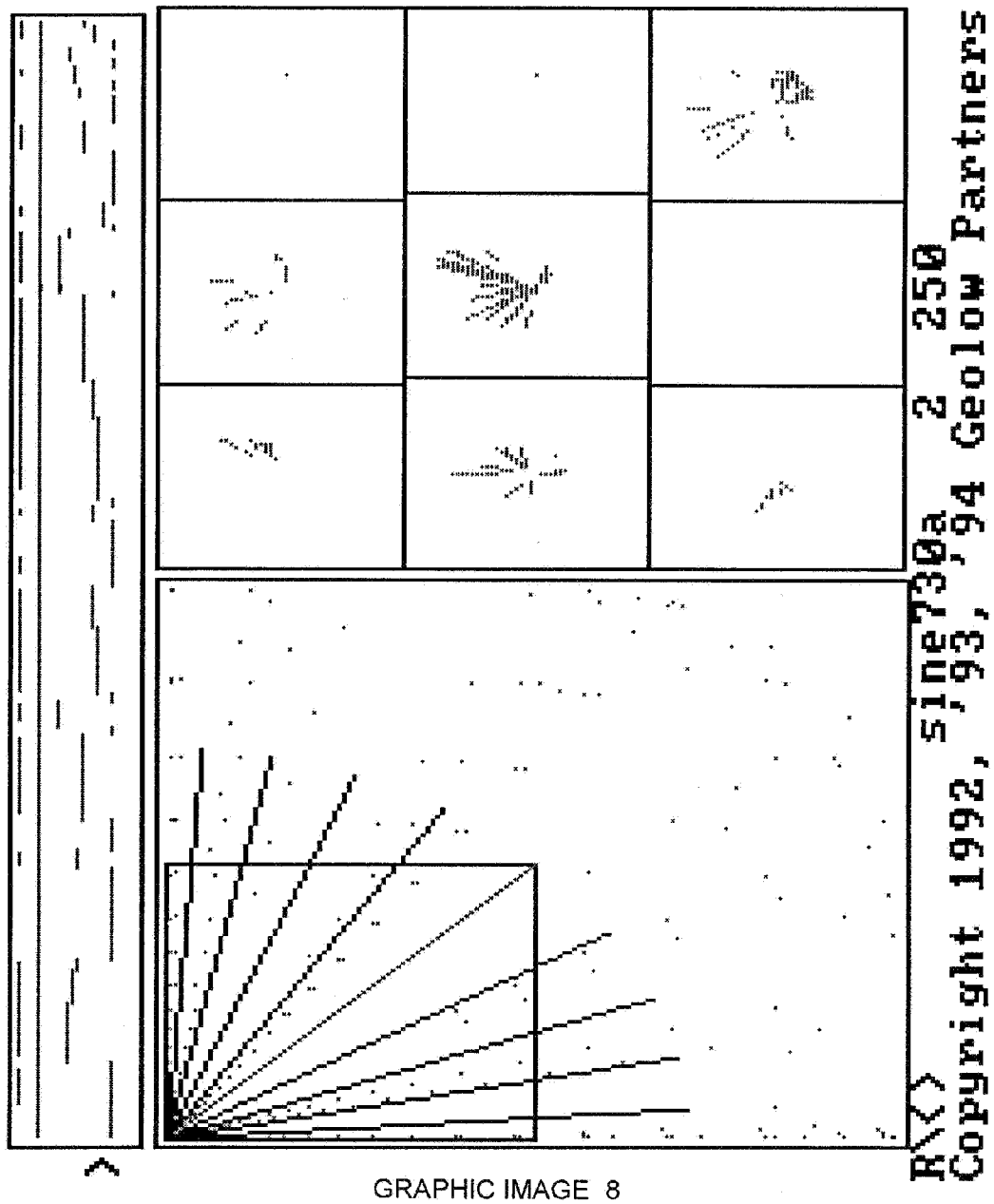

The term "pattern" as used in this specification has broad meaning, and includes more than obvious geometric regularity in features. For example, a definitive feature of fractals is that they display self-similarity at multiple scales. Thus, a search for a fractal pattern would include looking for multi-scale self-similarity. Plots of dynamic systems sometimes display apparent periodicities or quasi-orbits suggestive of underlying attractors. See Schlesinger, M. F.; Zaslavsky, G. M.; Klafter, J. "Strange Kinetics", Nature, vol. 363, pp. 31-37, 6 May 1993 for plotted examples of "patterns" in which non-random attractors were employed to create plotted figures where the created figures do not necessarily display obvious geometric regularities in the Euclidean sense, yet obey the constraints of underlying attractors. See especially FIG. 2, p. 33 for a plotted trajectory of a Levy walk interspersed with Levy flights. Mere incompleteness in a fractal image generated by mapped signal values, however, does not necessarily equate to a non-random pattern. This, in principle, is because the incompleteness may simply be due to an insufficient number of mapped signal values. The weaker the underlying attractor's effect on the signal, the more mapped points may be necessary for the pattern of the weak 'attractor' to appear. Nonetheless, some signal streams display strongly dominant patterns in a relatively small number of mapped signal values and therefore readily lend themselves to identification and segregation by the method of the present invention. Thus, the patterns are identified and segregated with relatively high efficiency in computer processing. It should be apparent that visual recognition of more complex "patterns" for confinement by selection sets using the present invention is a skill which can be learned, as can the appropriate application of selection sets to confine the visually-identified patterns. That is why the invention is viewed by the inventors as a signal-analysis tool.

We claim:

1. A machine which comprises:

A computer or other programmable apparatus whose actions are directed, by a computer program or other form of software, to map streams of signal values $S_nD_1$, $S_nD_2$, $S_nD_3$, collected substantially simultaneously at discrete serial collection times $t_n$ for n=1, 2, 3 . . . n, from signal Detectors $D_1$, $D_2$ and $D_3$, representing collected electromagnetic signals, to enable identification of a pattern within such streams of signal values, by the following steps:
   a. Set a Contraction Factor F>1;
   b. Define a triangle TRI having vertices $V_1$, $V_2$ and $V_3$, to each of which is assigned a different signal Detector $D_1$, $D_2$, and $D_3$ selected from within the series $D_a$, $D_b$, $D_c$, . . . $D_n$;
   c. Receive the streams of signal values $S_nD1$, $S_nD2$, $S_nD3$, collected substantially simultaneously at discrete serial collection times $t_n$ for n=1, 2, 3 . . . n, from signal Detectors $D_1$, $D_2$ and $D_3$;
   d. Define initial signal values $\{S_0D_1=0, S_0D_2=0, S_0D_3=0\}$;
   e. Define a maximum number MAX of discrete serial signal value collection times $\{t_n=t_{MAX}\}$;
   f. Set an Initial Map Point {IMP} on or near Triangle TRI corresponding to time $t_0$ within a time series $t_n$, which Initial Map Point is defined to be $MP_0$ within a Map Point series $MP_n$, for n=0, 1, 2, 3, . . . MAX, and initially set Last Prior Map Point $\{MP_{n-1}\}$ equal to said Initial Map Point;
   g. Iterate for n=1, 2, 3, . . . MAX, the following steps:
      i. Calculate the absolute scalar changes {ABS} {Delta $S_nD_1$, Delta $S_nD_2$, and Delta $S_nD_3$} between successive signal values collected at serial Times $\{t_{n-1}$ and $t_n\}$ from each of three signal detectors $\{D_1, D_2,$ and $D_3\}$, said absolute scalar changes calculated as: {Delta $S_nD_1$=ABS ($S_nD_1 - S_{n-1}D_3$); Delta $S_nD_2$=ABS ($S_nD_2 - S_{n-1}D_2$); Delta $S_nD_3$=ABS ($S_nD_3 - S_{n-1}D_3$)};
      ii. Select the largest absolute scalar change from among said calculated absolute scalar changes {ABS} {Delta $S_nD_1$, Delta $S_nD_2$, and Delta $S_nD_3$} and identify the signal detector which collected said largest absolute scalar change;
      iii. Select as vertex $VS_n$ from among the three vertices $\{V_1, V_2,$ or $V_3\}$ on the triangle TRI that vertex to which has been assigned the signal detector $\{D_1, D_2,$ or $D_3\}$ so identified as having collected said largest absolute scalar change {ABS} {Delta $S_nD_1$, Delta $S_nD_2$, Delta $S_nD_3$} at $t_n$;
      iv. Plot a serial Map Point $\{MP_n\}$ along a line between said Last Prior Map Point $MP_{n-1}$ and the vertex $VS_n$, at a distance $DIST_n$ from the last prior Map Point $\{MP_{n-1}\}$ toward said vertex $VS_n$, said distance $DIST_n$ being a quotient calculated as: the absolute scalar {ABS} linear distance between the Last Prior Mapped Point $\{MP_{n-1}\}$ and the selected vertex $VS_n$, divided by the Contraction Factor F $\{DIST_n=ABS(MP_{n-1}-VS_n)/F\}$; and
      v. Increment n by 1 and return to step g.i until n=MAX.

2. A machine comprising:

The machine of claim 1 combined with

Means for displaying for visual inspection said map of streams of signal values.

3. A machine, as in claim 1, to enable identification of a subset of signal values corresponding to a pattern identified in a portion of a map of streams of electromagnetic signal values which has been formed by the machine of claim 1, further comprising:

A computing apparatus which implements the following steps:

Receive the map of the streams of signal values which has been formed by the machine of claim 1, and Form a selection set which confines the portion of said map of signal values that contains the pattern, and Identify, automatically, the subset of signal values which is mapped to said portion of the map so confined.

4. A machine as in claim 3 further comprising:

i. Means for visually displaying the selection set relative to the map, and ii. Computer means for adjusting which portion of the map is confined by the selection set.

5. A machine as in claim 3 further comprising:

Means for visually displaying the subset of signal values identified by the machine of claim 3.

6. A machine as in claim 3 which automatically identifies from streams of electromagnetic signal values a subset of signal values which corresponds to a predetermined pattern on a portion of a map of those signal values, further comprising:

The selection set of the machine of claim 3 automatically confines the portion of said map that corresponds to the predetermined pattern and automatically identifies the signal values which have been mapped to the said confined portion of said map.

7. A machine, as in claim 6, further comprising:

The predetermined pattern which is automatically confined is formed by a plurality of mapped signal values and approximates a ray focused upon a vertex of said triangle TRI.

8. A machine, as in claim 6, further comprising:

The predetermined pattern which is automatically confined is formed by a plurality of mapped signal values and approximates a band roughly perpendicular to a side of said triangle TRI.

9. A machine, as in claim 6, further comprising:

The predetermined pattern is the subset of mapped signal values which remain after segregation of all other mapped signal values that approximate any rays focused upon any vertices of said triangle TRI.

10. A machine, as in claim 6, wherein said selection set further comprises:

A rectangular selection set.

11. A machine, as in claim 6, wherein said selection set further comprises:

A wedge selection set.

12. A machine as in claim 1 further comprising:

The Contraction Factor F is selected within the range:

$2 > F > 1.$

13. A machine as in claim 1, further comprising:

The Contraction Factor F is selected within the range:

$1.7 > F > 1.15.$

14. A machine, as in claim 1, comprising:

A computing apparatus of claim 1 further implements the following steps:

Form a graphic phase space portrait of the streams of signal values $S_n D1, S_n D2, S_n D3$, collected substantially simultaneously at discrete serial collection times $t_n$ for n=1, 2, 3 ... n, from signal Detectors $D_1$, $D_2$ and $D_3$, by iterating the following steps for discrete serial collection times $t_n$ for n=1, 2, 3, ... n:

1. construct a graphic drawing point entity $P_n$ having as its drawing coordinates in space at least two of the respective signal values $S_n D1, S_n D2, S_n D3$;

2. construct a graphic drawing point entity $P_{n+1}$ having as its drawing coordinates in space at least two of the respective signal values $S_{n+1} D_2$, and $S_{n+1} D_3$;

3. construct a graphic drawing line entity $LI_n$ connecting and terminating at said two graphic drawing point entities $P_n$ and $P_{n+1}$.

15. A machine for forming a map, relative to an approximation of the attractor of a fractal, of streams of signal values representing collected electromagnetic signals to enable identification of a pattern within said stream of signal value, which comprises:

a. Computer means for receiving the streams of signal values;

b. Computer means for mapping the streams of signal values relative to an approximation of the attractor of a fractal.

16. A machine, as in claim 15, to enable identification of a subset of signal values which form a pattern in a portion of a map made by the machine of claim 15, further comprising:

Computer means for receiving the map formed by the machine of claim 15, and Selection set means implemented by use of a computer for confining the portion of said map which contains said pattern, and Identification means implemented by use of a computer for identifying the signal values which are mapped to the portion of said map so confined.

17. A machine as in claim 15 wherein said means for receiving a stream of signal values further comprises:

Means for signal collection.

18. A machine as in claim 15 further comprising:

The fractal having an attractor which is selected for approximation is one of the following:

i. A Sierpinski gasket;

ii. A Sierpinski carpet;

iii. A Menger sponge;

iv. A polar fractal; or v. A spherical fractal.

19. A process to enable identification of a pattern in streams of signal values representing collected electromagnetic signals by forming a contraction map of the streams of signal values, relative to an approximation of the attractor of a fractal, which comprises:

The following specific operational steps to be performed by use of a computer:

i. Receive the streams of signal values representing collected electromagnetic signals;

ii. Map the received streams of signal values relative to an approximation of the attractor of a fractal.

20. A process, as in claim 19, for identification of a subset of signal values which subset forms a pattern that appears in a portion of a map made by the process of claim 19, further comprising:

The following specific operational steps to be performed by use of a computer:
  i. Confine the portion of said map which contains the pattern, and
  ii. Identify the subset of signal values which are mapped to the portion of said map so confined.

21. A process, as in claim 20, for deconstructing a graphic phase space portrait constructed of graphic drawing entities depicting streams of collected electromagnetic signal values, $S_nD1$, $S_nD2$, $S_nD3$, collected substantially simultaneously at discrete serial collection times $t_n$ for n=1, 2, 3 . . . n, from signal Detectors $D_1$, $D_2$ and $D_3$, by reference to a subset of those streams of signal values which subset has been identified by the process of claim 20, comprising:

The following specific operational steps to be performed by use of a computer upon said streams of signal values $S_nD1$, $S_nD2$, $S_nD3$:

Step a. Form a graphic phase space portrait of the streams of signal values by the following steps:
  1. construct a graphic drawing point entity $P_1$ having as its drawing coordinates in space at least two of the respective signal values $S_1D_1$, $S_1D_2$, and $S_1D_3$;
  2. constructing a graphic drawing point entity $P_2$ having as its drawing coordinates in space at least two of the respective signal values $S_2D_1$, $S_2D_2$, and $S_2D_3$;
  3. constructing a graphic drawing line entity $LI_1$, connecting and terminating at said two graphic drawing point entities $P_1$ and $P_2$;

Step b. Iterate steps a.1, a.2 and a.3 of this claim with additional received signal values collected substantially simultaneously from at least two of said detectors $D_1$, $D_2$, and $D_3$, at least one of additional discrete signal times $t_3$, $t_4$, . . . $t_n$;

Step c. Map, relative to an approximation of the attractor of a fractal, the same received signal values which were used in steps a. and b. of this claim to compose the graphic phase space portrait;

Step d. Identify, by the process of claim 19, a subset of the received signal values which contains a pattern;

Step e. Identify the particular graphic drawing entities within the graphic phase space portrait formed in Steps a. and b. of this claim which were constructed from the same subset of signal values that was identified by the process of claim 19 pursuant to Step d. of this claim.

22. The machine of claim 3 further comprising:
software which directs said machine to make said selection set responsive to adjusting inputs from an operator.

23. A process, as in claim 20, for forming a graphic phase space portrait constructed of graphic drawing entities depicting a subset of signal values, which subset is identified by the process of claim 20 from streams of collected electromagnetic signal values, comprising:

The following specific operational steps to be performed by use of a computer:

Step a. Receive the streams of signal values $S_nD1$, $S_nD2$, $S_nD3$, collected substantially simultaneously at discrete serial collection times $t_n$ for n=1, 2, 3 . . . n, from signal Detectors $D_1$, $D_2$ and $D_3$;

Step b. Identify by the process of claim 20 a subset of the streams of signal values received in pursuant to Step a. of this claim;

Step c. Form a graphic phase space portrait, using said subset of the streams of signal values identified in Step b. of this claim, by the following steps:
  1. construct a graphic drawing point entity $P_n$ having as its drawing coordinates in space at least two of the respective signal values $S_nD_1$, $S_nD_2$, and $S_nD_3$;
  2. constructing a graphic drawing point entity $P_{n+1}$ having as its drawing coordinates in space at least two of the respective signal values $S_{n+1}D_1$, $S_{n+1}D_2$, and $S_{n+1}D_3$;
  3. constructing a graphic drawing line entity $LI_n$, connecting and terminating at said two graphic drawing point entities $P_n$ and $P_{n+1}$;

Step d. Iterate steps c.1, c.2 and c.3 of this claim with additional signal values from said subset identified in Step b. of this claim.

24. A process comprising:

The following specific operational steps to be performed by use of a computer:

Step 1. Set a Contraction Factor F>1;

Step 2. Define a triangle TRI having vertices $V_1$, $V_2$ and $V_3$, to each of which is assigned a different signal Detector $D_1$, $D_2$, and $D_3$ selected from within the series $D_a$, $D_b$, $D_c$, . . . $D_n$;

Step 3. Receive the streams of signal values $S_nD1$, $S_nD2$, $S_nD3$, collected substantially simultaneously at discrete serial collection times $t_n$ for n=1, 2, 3 . . . n, from signal Detectors $D_1$, $D_2$ and $D_3$;

Step 4. Define initial signal values $\{S_0D_1=0, S_0D_2=0, S_0D_3=0\}$;

Step 5. Define a maximum number MAX of discrete serial signal value collection times $\{t_n=t_{MAX}\}$;

Step 6. Set an Initial Map Point {IMP} on or near Triangle TRI corresponding to time $t_0$ within a time series $t_n$, which Initial Map Point is defined to be $MP_0$ within a Map Point series $MP_n$, for n=0, 1, 2, 3, . . . MAX, and initially set Last Prior Map Point $\{MP_{n-1}\}$ equal to said Initial Map Point;

Step 7. Iterate for n=1, 2, 3, . . . MAX, the following steps:
  vi. Calculate the absolute scalar changes {ABS} {Delta $S_nD_1$, Delta $S_nD_2$, and Delta $S_nD_3$} between successive signal values collected at serial Times $\{t_{n-1}$, and $t_n\}$ from each of three signal detectors $\{D_1, D_2,$ and $D_3\}$, said absolute scalar changes calculated as: {Delta $S_nD_1$=ABS $(S_nD_1-S_{n-1}D_1)$; Delta $S_nD_2$=ABS $(S_nD_2-S_{n-1}D_2)$; Delta $S_nD_3$=ABS $(S_nD_3-S_{n-1}D_3)$};
  vii. Select the largest absolute scalar change from among said calculated absolute scalar changes {ABS} {Delta $S_nD_1$, Delta $S_nD_2$, and Delta $S_nD_3$} and identify the signal detector which collected said largest absolute scalar change;
  viii. Select as vertex $VS_n$ from among the three vertices $\{V_1, V_2,$ or $V_3\}$ on the triangle TRI that vertex to which has been assigned the signal detector $\{D_1, D_2,$ or $D_3\}$ so identified as having collected said largest absolute scalar change {ABS} {Delta $S_nD_1$, Delta $S_nD_2$, Delta $S_nD_3$} at $t_n$;
  ix. Plot a serial Map Point $\{MP_n\}$ along a line between said Last Prior Map Point $MP_{n-1}$ and the vertex $VS_n$, at a distance $DIST_n$ from the last prior Map Point $\{MP_{n-1}\}$ toward said vertex $VS_n$, said distance $DIST_n$ being a quotient calculated as: the absolute scalar {ABS} linear distance between the Last Prior Mapped Point $\{MP_{n-1}\}$ and the selected vertex $VS_n$, divided by the Contraction Factor F $\{DIST_n$=ABS $(MP_{n-1}-VS_n)/F\}$; and
  x. Increment n by 1 and return to step g.i until n=MAX.

25. A process, as in claim 24, further comprising:

The steps of the process of claim 24 combined with the following specific operational step to be performed by use of a computer:

Step 8. Displaying for visual inspection said map of streams of signal values.

26. A process, as in claim 24, to enable identification of a subset of signal values corresponding to a pattern identified in a portion of a map of streams of electromagnetic signal values which has been formed by the process of claim 24, comprising:

The following specific operational steps to be performed by use of a computer:

Receive the map of the streams of signal values which has been formed by the process of claim 24, and Form a selection set which confines the portion of said map of signal values that contains the pattern, and Identify automatically the subset of signal values which is mapped to said portion of the map so confined.

27. A process comprising:

The process of claim 26 combined with the following specific operational steps to be performed by use of a computer:

Visually displaying the selection set relative to the map, and

Adjusting which portion of the map is confined by the selection set.

28. A process comprising:

The process of claim 26 combined with the following specific operational steps to be performed by use of a computer:

Visually displaying the subset of signal values identified by the process of claim 26.

29. A process, as in claim 26, which automatically identifies from streams of electromagnetic signal values a subset of signal values which corresponds to a predetermined pattern on a portion of a map of those signal values, comprising:

The process of claim 26 combined with the following specific operational steps to be performed by use of a computer:

Employing a predetermined selection set which automatically confines the portion of said map that corresponds to the predetermined pattern and automatically identifies the subset of signal values that are mapped to the portion of said map so confined.

30. A process for forming a map, relative to an approximation of the attractor of a fractal, of streams of signal values representing collected electromagnetic signals to enable identification of a pattern within said stream of signal values, which comprises:

The following specific operational steps to be performed by use of a computer:

a. Receiving the streams of signal values;

b. Mapping the streams of signal values relative to an approximation of the attractor of a fractal.

31. A process, as in claim 30, to enable identification of a subset of signal values which form a pattern in a portion of a map made by the process of claim 30, further comprising:

The following specific operational steps to be performed by use of a computer:

Receiving the map formed by the process of claim 30, and Confining the portion of said map which contains said pattern, Identifying the signal values which are mapped to the portion of said map so confined.

32. A process comprising:

The process of claim 30 combined with the following specific operational steps to be performed on or with the aid of a computer:

Approximating a fractal having an attractor which is selected from one of the following:

i. A Sierpinski gasket;

ii. A Sierpinski carpet;

iii. A Menger sponge;

iv. A polar fractal; or v. A spherical fractal.

* * * * *